United States Patent [19]

Pinchuk

[11] Patent Number: 5,163,958
[45] Date of Patent: Nov. 17, 1992

[54] CARBON COATED TUBULAR ENDOPROSTHESIS

[75] Inventor: Leonard Pinchuk, Miami, Fla.

[73] Assignee: Cordis Corporation, Miami Lakes, Fla.

[21] Appl. No.: 746,301

[22] Filed: Aug. 13, 1991

Related U.S. Application Data

[63] Continuation of Ser. No. 305,525, Feb. 2, 1989, abandoned.

[51] Int. Cl.⁵ ............................................. A61F 2/02
[52] U.S. Cl. .................................... 623/11; 606/194; 606/198
[58] Field of Search ............... 623/1, 11, 12; 604/96, 604/104; 606/191, 194, 198; 267/87, 165, 167, 170

[56] References Cited

U.S. PATENT DOCUMENTS

| | | | |
|---|---|---|---|
| 3,526,005 | 9/1970 | Bokros | 128/92 R |
| 3,969,130 | 7/1976 | Bokros | 623/2 |
| 4,074,718 | 2/1978 | Morrison, Jr. | |
| 4,101,984 | 7/1978 | MacGregor | |
| 4,149,277 | 4/1979 | Bokros | 623/13 |
| 4,164,045 | 8/1979 | Bokros et al. | 623/1 |
| 4,281,669 | 8/1981 | MacGregor | |
| 4,503,569 | 3/1985 | Dotter | 128/343 |
| 4,542,752 | 9/1985 | DeHaan et al. | |
| 4,553,545 | 11/1985 | Maass et al. | |
| 4,580,568 | 4/1986 | Gianturco | |
| 4,693,721 | 9/1987 | Ducheyne | |
| 4,733,665 | 3/1988 | Palmaz | |
| 4,776,337 | 10/1988 | Palmaz | 623/1 |
| 4,800,882 | 1/1989 | Gianturco | 128/343 |
| 4,886,062 | 12/1989 | Wiktor | 128/343 |

FOREIGN PATENT DOCUMENTS

| | | | |
|---|---|---|---|
| 1068052 | 12/1979 | Canada | 623/1 |
| 312852 | 4/1989 | European Pat. Off. | |

OTHER PUBLICATIONS

Schoen, "Carbon Heart Valve Prostheses", *Carbon Heart Valves*, Chap. 11, pp. 249-261.

*Primary Examiner*—Randy C. Shay
*Attorney, Agent, or Firm*—Lockwood, Alex, Fitzgibbon & Cummings

[57] ABSTRACT

An elongated tubular endoprosthesis or stent is provided which includes a carbon coated surface that is antithrombogenic and helps to restrain the metal body member of the endoprosthesis in the event of a fracture thereof. By providing a suitable underlayer surface to which the carbon coating generally conforms, the stent presents a porous surface to a blood vessel or the like within which it is designed to be implanted. This porous carbon surface promotes ingrowth of tissue thereinto during implantation of the endoprosthesis.

5 Claims, 2 Drawing Sheets

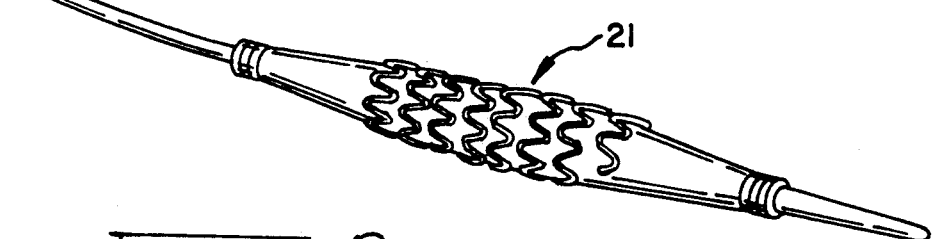
FIG_1_
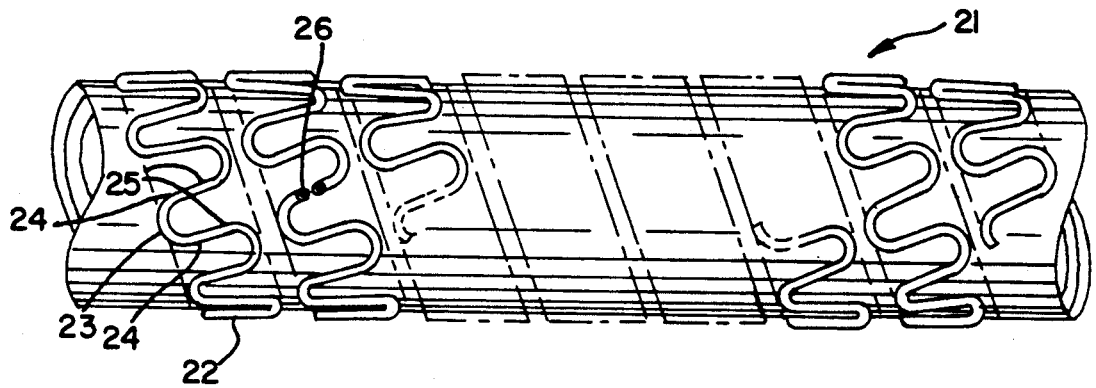
FIG_2_
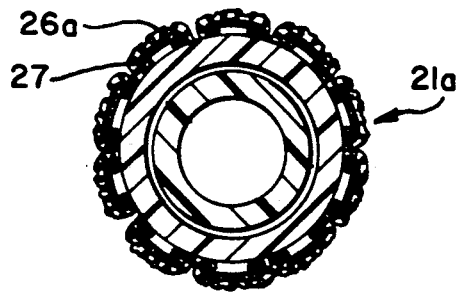
FIG_3_
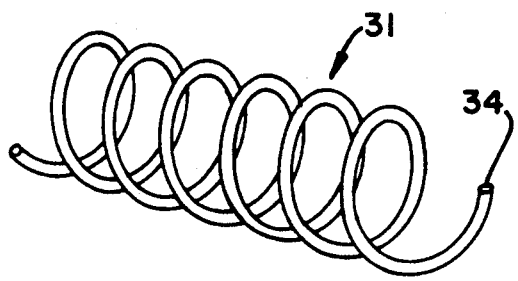
FIG_4_
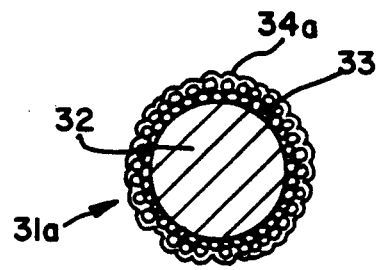
FIG_5_

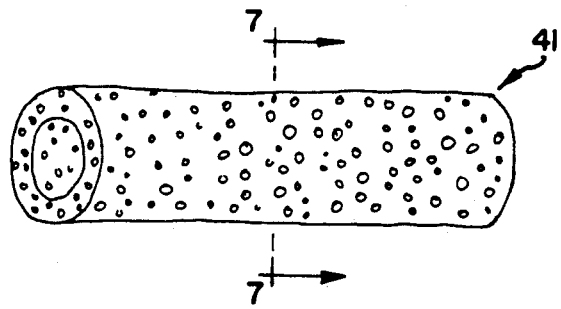
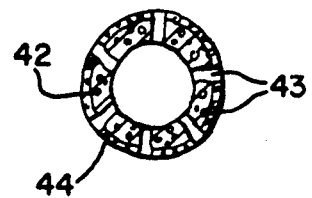
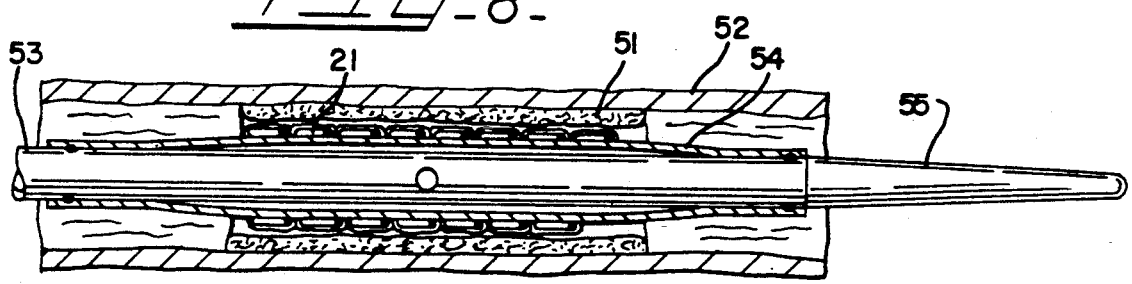
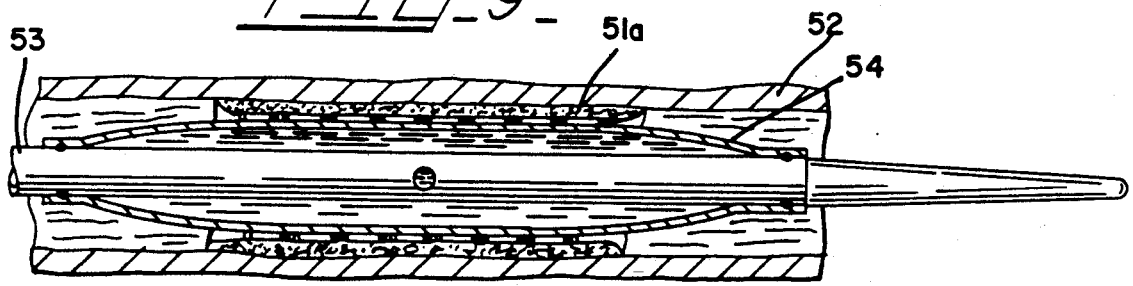
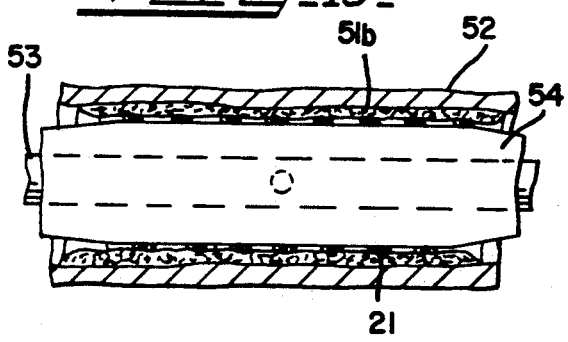
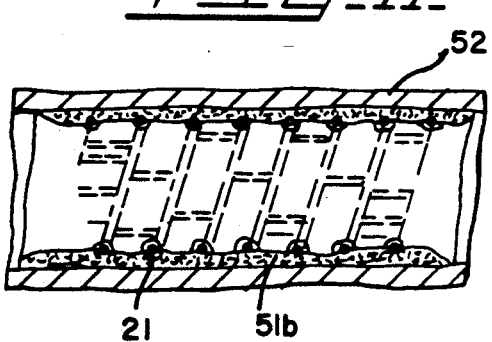

CARBON COATED TUBULAR ENDOPROSTHESIS

This application is a continuation of application Ser. No. 305,525, filed Feb. 2, 1989, now abandoned.

BACKGROUND AND DESCRIPTION OF THE INVENTION

The present invention generally relates to endoprosthesis devices and to a method for making same. More particularly, the invention relates to a generally tubular endoprosthesis that includes a pyrolytic amorphous carbon layer The carbon-layered surface of the endoprosthesis presents an antithrombogenic interface with the tissue within which it is implanted. This interface renders the endoprosthesis less thrombogenic and can be useful in restraining the endoprosthesis in the event of its fracture while implanted. The carbon layer itself also protects the underlying metallic surface from degradation. The endoprosthesis may be of the type that is radially expandable between a generally unexpanded insertion circumference and an expanded implantation circumference which is greater than the unexpanded insertion circumference. When the endoprosthesis is of a type having an underlying substrate with a relatively large surface area, the carbon coating can be especially useful in maintaining patency.

Endoprostheses are known for treating stenoses, stricture, aneurysm conditions and the like. An endoprosthesis device of this type, which is at times referred to as a stent, is typically placed or implanted by a mechanical transluminal procedure. Often a device of this type is percutaneously implanted within the vascular system to reinforce collapsing, partially occluded, weakened and/or abnormally dilated localized sections of a blood vessel or the like. Stents of this general type can also be used in the urinary tract, the bial tract, the intestinal tract and the like. When endoprostheses or stents are used to treat a stenosis condition, typically such is done in association with a dilation element such as an angioplasty balloon. In this situation, the dilation element or balloon device opens the constriction, and the stent or the like is positioned thereat in order to prevent or at least substantially slow re-formation of the stenosis.

Generally speaking, currently available conventional stents present an implantation interface that is smooth and generally rigid, often being made of stainless steel or other metal. Typically, these structures present an implantation interface that is inherently thrombogenic. After implantation, loosely adhered tissue will surround such conventional stents or tubular endoprostheses, and this loose tissue will be constantly traumatized by motion of the blood vessel wall. Besides presenting a generally thrombogenic surface, stents of this type are typically constructed of wire materials that can degrade during extended implantation periods.

Another attribute of many stents is that they are radially compressible and expandable so they will easily pass through blood vessels or the like when they are collapsed and will expand to an implanted size after the stenosis, aneurysm or the like has been reached. It is also generally desirable that a stent be substantially flexible throughout its length so that it is easily maneuverable through bends and curves of the blood vessel or the like. These desirable flexibility and maneuverability attributes can themselves lead to potential problems. Relative motion between the surface of the stent and the vessel or the like within which it is implanted can lead to trauma of the blood vessel and/or can contribute to conditions under which a portion of a stent, particularly one including thin wire components, may fracture.

Currently known stent products have a variety of different structures. Included are those which are essentially coiled springs. When this type of spring stent is tightly coiled, its diameter is relatively small for insertion through a blood vessel or the like. When the coil is sprung or coiled more loosely, the stent assumes its expanded, implantation orientation. Maass et al U.S. Pat. No. 4,553,545 is illustrative of this type of coiled spring stent or endoprosthesis. Multihelix or braided stents are also known. Palmaz U.S. Pat. No. 4,733,665 is representative of an expandable stent of this general type. Gianturco U.S. Pat. No. 4,580,568 illustrates a percutaneous endovascular stent formed of stainless steel wire that is arranged in a closed zig-zag pattern. Another type of stent is known as a Statz stent, and it includes a hypodermic tube with longitudinal slots etched into its body.

The respective implantation interfaces that are provided by these typical types of stent structures are usually generally smooth metallic surfaces. With some of these structures, the metallic surface is provided in the form of thin wires that can be relatively widely spaced apart. While stents of this general type have many advantageous properties, particularly from the point of view of their flexibility and maneuverability, they can present a situation in which the stent has an implantation interface that includes relatively widely spaced longitudinal edges of thin and smooth metal wires. It is, of course, important to minimize potential trauma that can develop during long term implantation of these types of devices.

The present invention retains most of the advantageous features of the various stents or tubular endoprostheses such as those discussed herein. At the same time, various deficiencies of these types of structures are avoided, while important and advantageous features are realized In summary, the generally tubular endoprosthesis of this invention includes a generally cylindrical metallic body member having a pyrolytic amorphous carbon layer on at least the outwardly facing surface thereof. When desired, the generally cylindrical metallic body member has a porous surface, and a porous carbon surface is defined when pyrolytic amorphous carbon is coated thereover.

It is a general object of the present invention to provide an improved generally tubular endoprosthesis.

Another object of the present invention is to provide an improved endoprosthesis or stent having an amorphous carbon layer on at least its outer surface.

Another object of the present invention is to provide an improved endoprosthesis or stent which has an outside surface of carbon coated over a porous substrate to thereby present a porous interface during implantation.

Another object of this invention is to provide an improved endoprosthesis or stent that has enhanced antithrombogenic properties.

Another object of this invention is to provide an improved endoprosthesis or stent that is protected from degradation upon implantation.

Another object of the present invention is to provide a improved carbon-coated endoprosthesis for transluminal implantation and that has very large radial expansion capabilities.

Another object of this invention is to provide an improved endoprosthesis or stent which is radially expandable by an expanding member or balloon of a catheter device.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 1 is a perspective view illustrating an embodiment of a tubular endoprosthesis according to the present invention positioned on a balloon of a transluminal catheter;

FIG. 2 is an enlarged detail view, partially broken away, of the stent and balloon illustrated in FIG. 1;

FIG. 3 is a transverse cross-sectional view through a stent and balloon having an overall structure according to FIG. 2 and in which a porous underlayer also is included;

FIG. 4 is an illustration of another embodiment of a carbon-coated endoprosthesis suitable for percutaneous transluminal implantation;

FIG. 5 is a transverse cross-sectional view through a strand of a stent having an overall configuration as shown in FIG. 4 and in which a porous underlayer also is shown;

FIG. 6 is a perspective illustration of a further type of endoprosthesis;

FIG. 7 is a cross-sectional view along the line 7—7 of FIG. 6;

FIG. 8 is an illustration, partially in longitudinal cross-section, of a stent and balloon assembly of the type generally illustrated in FIG. 1 positioned at an implantation site;

FIG. 9 is an illustration, partially in cross-section, showing expansion of the stent shown in FIG. 8;

FIG. 10 is an illustration similar to that of FIG. 9 and that depicts additional balloon expansion; and FIG. 11 is a view similar to FIG. 10 after removal of the balloon catheter.

DESCRIPTION OF THE PARTICULAR EMBODIMENTS

FIGS. 1, 2, 3, 8, 9, 10 and 11 illustrate an especially advantageous embodiment of the present invention. A radially expandable endoprosthesis or stent is generally designated as 21. Stent 21 includes a plurality of generally circumferential sections 22. In this illustrated embodiment, each of the circumferential sections 22 are formed from the same continuous, substantially helically wrapped length, such as the undulating length shown in FIGS. 1 and 2.

At least one of the circumferential sections 22 includes at least one expandable segment 23, which is a bendable member that typically includes one or more legs 24. Each leg 24 is bendably secured to the rest of the circumferential section 22 by a so-called living joint or hinge which is a unitary or integral component of the leg 24 and the adjacent portion circumferential section 22. For example, in this illustrated embodiment, each leg 24 is bendably joined to another leg through an integral or living hinge having a generally arcuate shape. When the stent 21 expands, end portions 25 of the respective legs 24 move farther apart, thereby increasing the circumference and diameter of the stent 21, to a position such as the one generally shown in FIG. 9.

The stent 21 illustrated in FIGS. 1 and 2 is a shaped and wound continuous metal wire which has a coating or layer of pyrolytic amorphous carbon 26 over the outside surface of the wire. FIG. 3 illustrates a stent 21a which has carbon layer 26a that can allow ingrowth of tissue into the wire after implantation has proceeded. This porosity of the layer 26a can be achieved, for example, by providing an underlayer 27 of sintered beads or fine wire winding or braiding onto the continuous wire from which the stent 21a is made.

Referring more particularly to the pyrolytic amorphous carbon layer, the identity and general properties of this material will be understood by those skilled in the art and is generally similar to material used on artificial heart valves and the like. The pyrolytic amorphous carbon of this layer lacks a definite crystal structure and is obtained by thermal decomposition of a carbon material. Layer 26, 26a itself is a dense, substantially non-porous carbon network that is stronger and more resistant to degradation than other carbon coatings and is generally impermeable to all fluids. It tolerates bending action to a greater degree than, for example, vitreous carbon. The amorphous nature of the carbon facilitates its ability to provide the porous carbon surface 26a by generally following the porosity of the underlayer 27 when it is included as shown in FIG. 3 for example.

With more particular reference to the underlayer such as that shown at 27 in FIG. 3, this provides a desirable porous or textured surface to the stent 21a. When underlayer 27 takes the form of beads sintered to the surface of the stent body, same can be on the order of the sintered porous surface as described in MacGregor U.S. Pat. No. 4,101,984, the subject matter thereof being incorporated hereinto. A plurality of fine mesh metal particles are suitably positioned on the stent body by the use of a binder or the like. Thereafter, sintering is conducted so as to cause metal fusion interconnection of these fine metal particles with one another and with the surface of the stent body. The result is the formation of a rigid porous structure having a network of interconnected pores substantially uniformly distributed on the surface of the stent body. Generally speaking, the porosity of the underlayer 27 can vary between about 10 percent and about 50 percent of the underlayer coating. Pore size is chosen to promote the type of tissue ingrowth or endothelialization that is desired. Generally, the interstitial pore size provided by the underlayer 27 is less than about 200 microns.

When the underlayer 27 takes the form of a fine wire that is wound or braided onto the surface of the stent body, this can be achieved by a procedure similar to that described herein with respect to bead sintering, except the particles that are thereby sintered are generally elongated metallic fibers. An example of an approach in this regard is Ducheyne U.S. Pat. No. 4,693,721, incorporated by reference hereinto.

The stent body itself will typically be made from a smooth metal such as a wire made of ELIGILOY (trademark) metal or an alloy such as NP36N. The combination of the porous underlayer 27 and the pyrolytic amorphous carbon layer 26a allows for tissue ingrowth and endothelialization into the stent material itself, rather than only between components of the stent body, as would be the case for a stent that does not include the porous surface. This porous coating is advantageous inasmuch as it is less thrombogenic when implanted than is a conventional smooth wire stent or the like. In addition, this coating helps to restrain the wire stent in the event that the wire develops a fracture. The carbon coating provides both a well-established antithrombogenic surface, and it also protects the metal wire of the stent from degrading over time.

With more particular reference to the endoprosthesis or stent that is illustrated in FIGS. 1, 2, 3, 8, 9, 10 and 11, it is preferably made in the following manner. A strand of elongated metal such as a wire is generally tightly wound around a mandrel, preferably one that is generally rectangular in shape and has rounded edges. Preferably, this winding is carried out in a manner such that there is substantial spacing between each individual wind of the strand, after which the mandrel is removed from the thus wound strand. The three-dimensionally wound strand is then subjected to flattening forces so that it is transformed into a generally planar or two-dimensional shape including a plurality of expandable segments 23 that are joined end to end. The forces may be applied by any suitable means. For example, the wound strand can be compressed between two planar surfaces, during which procedure portions of the wound strand are twisted until the generally uni-planar undulating length is formed, which length has a generally sinusoidal character.

The undulating length is then wound, in a generally helical manner, around a substantially cylindrical mandrel This generally helical wrapping procedure continues until the desired number of circumferential sections 22 are formed in order to provide the radially expandable stent 21 of the desired length. It may, depending upon the type of wire used, be necessary to heat anneal the helically wound stent 21.

The particular shape of the undulating configuration of the stent 21 that is illustrated in FIG. 2 is prepared by initially winding on the rounded edge rectangular cross-section mandrel referred to hereinabove. Mandrels having differing shapes can be used to prepare stents having differently shaped expandable segments For example, a rectangularly shaped mandrel would prepare undulations having adjoining sections that are generally perpendicular to each other. An oval-shaped or elliptically shaped mandrel would prepare expandable segments that are generally Z-shaped. Somewhat differently sized generally Z-shaped sections also would be prepared with a mandrel having a round cross-section.

Regarding the embodiments illustrated in FIGS. 4 and 5, an endoprosthesis or stent 31 is shown. Stent 31 is of the type which embodies a coiled wire that will radially expand by a twisting movement which also longitudinally reduces the length of the stent 31. Stent 31 includes a coiled metal wire 32 having a pyrolytic amorphous carbon coating 34 thereover that presents a generally antithrombogenic surface which also provides degradation protection attributes of the type discussed herein As shown in FIG. 5, stent 31a includes an underlayer 33 of sintered beads or strands or the like of the type discussed herein in connection with the FIG. 3 embodiment. Carbon coating 34a overlies this porous underlayer 33 in order to thereby present a porous carbon layer. In this manner, a wire having a porous carbon surface is provided which promotes endothelialization and tissue ingrowth.

Concerning the embodiment illustrated in FIGS. 6 and 7, a stent 41 is provided which embodies a porous tube having a carbon-coated surface. More particularly, stent 41 includes a metal tubular member 42 having a plurality of pores 43 therewithin and/or therethrough.

A pyrolytic coating of amorphous carbon 44 generally conforms to the porous surface of the metal tubular member 42, and a porous carbon coated external surface is provided. Without the amorphous carbon layer 44, a large surface area stent such as stent 41 would plug up after implantation, whereas the carbon coating 44 on stent 41 enhances its patency.

FIGS. 8, 9, 10 and 11 illustrate an implantation arrangement which is especially suitable for a stent such as those illustrated in FIGS. 1, 2 and 3. A stenosis or lesion 51 within a blood vessel 52 is transluminally reached by a balloon catheter 53 having a stent 21 overlying a collapsed balloon 54 of the catheter 53, which has a suitable tip portion 55. The balloon 54 is then expanded in a well-known manner, at which time the stent 21 is also expanded by opening the expandable segments thereof. An intermediate dilation position is shown in FIG. 9, and an initially dilated lesion 51a is shown therein. FIG. 10 shows additional dilation by the balloon 54, and the thus treated lesion 51b is also shown The stent 21 remains in place as generally illustrated in FIG. 11 because the material of the expanded stent 21 exerts a hoop stress when it is expanded to the size illustrated in FIG. 11 such that it will not collapse by inwardly directed radial forces presented by the treated lesion 51b and vessel wall 52 or the like.

For purposes of illustration, a typical collapsed or insertion outer diameter for a stent of the type generally discussed herein is about 0.085 inch, with the inner diameter thereof being on the order of about 0.075 inch. The overall length of the stent is selected so as to be adequate for that generally needed to treat the lesion or the like, taking into consideration any change in length that might be experienced by the particular stent structure, such as the one illustrated in FIGS. 4 and 5. A typical expanded diameter of a radially expandable stent is about 0.24 inch outside diameter and a 0.23 inch inside diameter An expansion ratio for the stent structures illustrated in FIGS. 1, 2 and 3 is approximately 2.8.

It will be understood that the embodiments of the present invention which have been described are illustrative of some of the applications of the principles of the present invention. Numerous modifications may be made by those skilled in the art without departing from the true spirit and scope of the invention.

I claim:

1. A generally tubular endoprosthesis, comprising:
   a generally cylindrical metallic body member having an inside lumen surface and outside surface means for engaging and for reinforcing a collapsing, partially occluded, weakened or abnormally dilated section of a blood vessel, said generally cylindrical metallic body member being an elongated flexible metallic strand which is configured into a plurality of generally circumferential strand sections which are continuous with one another;
   an underlayer of rigid beads sintered to each other and to said elongated flexible metallic strand, which sintered rigid beads provide a flexible, porous, textured surface having a network of interconnected pores;
   a pyrolytic amorphous carbon layer coating said underlayer of sintered rigid beads and said elongated flexible metallic strand and flexing therewith said flexible, porous, textured surface of the rigid beads supporting said pyrolytic amorphous carbon layer coating such that said pyrolytic amorphous carbon layer coating overlies said rigid beads and said network of interconnected pores and generally follows the contour of the rigid beads and the network of interconnected pores;

said generally cylindrical metallic body member, said underlayer of rigid beads and said pyrolytic amorphous carbon layer coating cooperate to define an antithrombogenic and flexible generally tubular endoprosthesis having pore means for promoting ingrowth of tissue thereinto during implantation of the endoprosthesis; and said underlayer of rigid beads and said pyrolytic amorphous carbon layer coating substantially covering at least said outside surface means to thereby restrain said elongated flexible metallic strand in the event of fracture of one or more sections of the elongated metallic strand.

2. The endoprosthesis according to claim 1, wherein said generally cylindrical metallic body member includes a coiled wire, and said pyrolytic amorphous carbon layer coats said coiled wire.

3. The endoprosthesis according to claim 1, wherein said generally circumferential strand sections are substantially adjacent to one another and generally axially oriented with respect to each other;

at least one of said generally circumferential strand sections having an expandable segment which imparts radial expandability wherein said section has an unexpanded insertion circumference and an expanded implantation circumference which is greater than said unexpanded insertion circumference; and said expandable segment of the generally circumferential section is a generally foldable member that is bendable between a generally closed orientation and a generally opened orientation so as to impart radial expandability to the generally circumferential section and to said generally cylindrical metallic body member.

4. The endoprosthesis according to claim 1, wherein said generally cylindrical metallic body member includes a coiled wire.

5. The endoprosthesis according to claim 1, wherein said generally cylindrical metallic body member includes a metal tubular member having pores.

* * * * *

UNITED STATES PATENT AND TRADEMARK OFFICE
CERTIFICATE OF CORRECTION

PATENT NO. : 5,163,958
DATED : November 17, 1992
INVENTOR(S) : Leonard Pinchuk

It is certified that error appears in the above-indentified patent and that said Letters Patent is hereby corrected as shown below:

```
Col. 2, line 41, "realized In" should read --realized.  In--;
      line 66, "a" should read --an--.
Col. 4, line 60, "metal or" should read --metal alloy or--.
Col. 5, lines 27-28, "mandrel This" should read --mandrel.  This--;
      line 39, "segments For" should read --segments.  For--;
      line 56, "herein As" should read --herein.  As--.
Col. 6, line 20, insert a period --.-- after "shown"; line 64,
      insert a comma --,-- after "therewith".
Col. 8, line 5, "wherein" should read --whereby--.
```

Signed and Sealed this

Seventh Day of February, 1995

*Attest:*

BRUCE LEHMAN

*Attesting Officer*   *Commissioner of Patents and Trademarks*